(12) United States Patent
Gillberg et al.

(10) Patent No.: US 11,533,862 B2
(45) Date of Patent: Dec. 27, 2022

(54) METHOD AND SYSTEM FOR SELECTING A PLANT VARIETY

(71) Applicant: Yield Systems Oy, Helsinki (FI)

(72) Inventors: Jussi Gillberg, Aalto (FI); Samuel Kaski, Aalto (FI); Pekka Marttinen, Aalto (FI); Hiroshi Mamitsuka, Aalto (FI)

(73) Assignee: Yield Systems Oy, Helsinki (FI)

( * ) Notice: Subject to any disclaimer, the term of this patent is extended or adjusted under 35 U.S.C. 154(b) by 567 days.

(21) Appl. No.: 16/624,584

(22) PCT Filed: Jun. 25, 2018

(86) PCT No.: PCT/FI2018/050493
§ 371 (c)(1),
(2) Date: Dec. 19, 2019

(87) PCT Pub. No.: WO2018/234639
PCT Pub. Date: Dec. 27, 2018

(65) Prior Publication Data
US 2020/0128769 A1    Apr. 30, 2020

(30) Foreign Application Priority Data
Jun. 22, 2017 (FI) ..................................... 20175589

(51) Int. Cl.
*A01H 1/04* (2006.01)
*G16B 20/00* (2019.01)
(Continued)

(52) U.S. Cl.
CPC .............. *A01H 1/04* (2013.01); *C12Q 1/6895* (2013.01); *G16B 20/00* (2019.02); *G16B 20/20* (2019.02); *G16B 40/20* (2019.02); *C12Q 2600/13* (2013.01)

(58) Field of Classification Search
CPC .......... A01H 1/04; G16B 20/20; G16B 20/00; G16B 40/20; C12Q 1/6895; C12Q 2600/13
See application file for complete search history.

(56) References Cited

U.S. PATENT DOCUMENTS 11,107,551 B2 * 8/2021 Buntjer .................. G16B 20/00
11,174,522 B2 * 11/2021 Baumgarten .......... G16B 40/30
(Continued)

OTHER PUBLICATIONS

Juan Burgueno et al "Genomic Prediction of Breeding Valueds when Modeling Genotype x Environment Interactions using Pedigree and Dense Molecular Markers", Crop Science, vol. 52, No. 2, Jan. 1, 2012, DOI: 10.2135/cropsci2011.06.0299, 14 pages.
(Continued)

*Primary Examiner* — Gregory M Desire
(74) *Attorney, Agent, or Firm* — Ziegler IP Law Group, LLC

(57) ABSTRACT

A method of selecting a plant variety for cultivation in a target area includes selecting a selection score function; estimating values of a first set of environmental parameters for a predefined future period of time for the target area and receiving a set of phenotype information including phenotypic trait measurements for a first sub-set of a plurality of plant varieties and a set o environmental parameters for said first sub-set. Furthermore, the method includes determining a prediction model for the phenotypic traits; using the prediction model to output predictions for phenotypic traits for the plurality of chosen plant varieties; using the selection score function to compute selection score values; and selecting at least one plant variety to be cultivated in the target area from the plurality of chosen plant varieties, based the computed selection score values of the plurality of chosen plant varieties.

13 Claims, 1 Drawing Sheet

(51) Int. Cl.
G16B 40/20 (2019.01)
C12Q 1/6895 (2018.01)
G16B 20/20 (2019.01)

(56) References Cited

U.S. PATENT DOCUMENTS

| | | | | |
|---|---|---|---|---|
| 2010/0145624 | A1* | 6/2010 | Kishore | G16B 20/00 702/19 |
| 2011/0296753 | A1* | 12/2011 | Guo | G16B 20/40 702/19 |
| 2019/0174691 | A1* | 6/2019 | Chavali | G16B 40/20 |
| 2021/0022303 | A1* | 1/2021 | Cao | A01C 1/00 |

OTHER PUBLICATIONS

Margo Lopez-Cruz et al. "Increased Prediction Accuracy in Wheat Breeding Trials Using a Marker x Environment Interaction Genomic Selection Model", Genes Genomes Genetics, vol. 5, No. 4, Feb. 6, 2015, DOI: 10.1534/g3.114.016097, 36 pages.

Osval A Montesinos-Lopez et al "Predicting grain yield using canopy hyperspectral reflectance inwheat breeding data", Plant Methods vol. 13, Jan. 3, 2017, DOI: 10.1186/s13007-016-0154-2, 24 pages.

Jarquin Dieg et al, "A reaction norm model for genomic selection using high-dimensional genomic and environmental data", Theoretical and applied genetics: International Journal of Plant Breeding Research, Springer, Berlin, DE, vol. 127, No. 3, Dec. 12, 2013, ISSN: 0040-5752, DOI: 10.1007/S00122-013-2243-1, 14 pages.

Crossa Jose et al, "Genomic Selection in Plant Breeding: Methods, Models, and Perspectives", Trends in Plant Science, vol. 22, No. 11, Nov. 1, 2017, ISSN: 1360-1385, DOI: 10.1016, 16 pages.

Abelardo Montesinos-Lopez et al., "Genomic Bayesian functional regression models withinteractions forpredicting wheat grain yield using hyper-spectral image data Plant Methods", Plant Methods, vol. 13, Jul. 27, 2017, DOI: 10.1186/s13007-017-0212-4, 30 pages.

International Search Report and Written Opinion, Application No. PCT/FI2018/050493, dated Sep. 4, 2018, 13 pages.

Gillberg et al Modelling GxE with historical weather information improves genomic prediction in new environments, first posted online Nov. 2, 2017, doi: http://dx.doi.org/10.1101/213231, 30 pages.

* cited by examiner

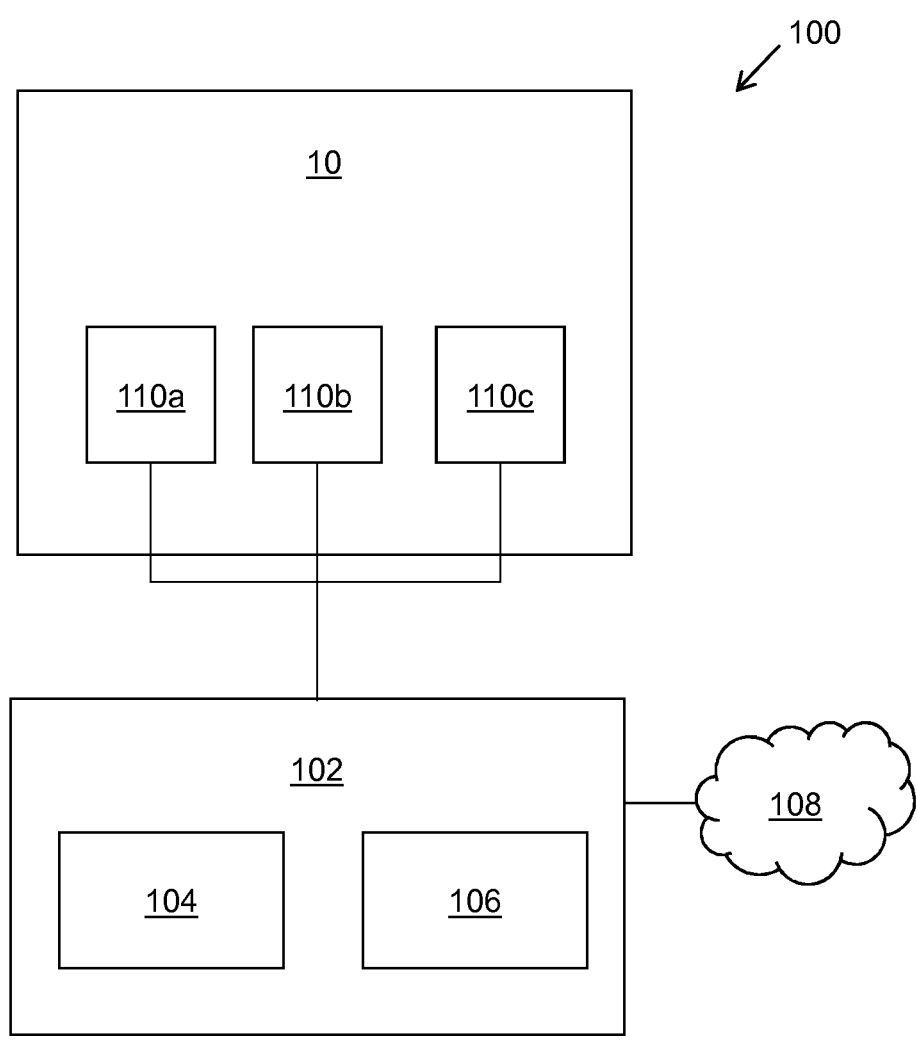

METHOD AND SYSTEM FOR SELECTING A PLANT VARIETY

TECHNICAL FIELD

The present disclosure relates generally to plant cultivation and more specifically to methods and systems for selecting a plant variety for cultivation in a target area. The present disclosure further relates generally to plant breeding and more specifically to methods and systems for selecting a plant line when breeding new varieties for a target area. The present disclosure still further relates to use of a system as described below.

BACKGROUND

The impact of the environment on plant growth and agronomic traits has been investigated both scientifically and commercially substantially. Plants have adapted differently to geographic locations and more generally environmental conditions both naturally and due to plant breeding, and plants have incorporated changes in their genetic makeup resulting in substantially different plant varieties. It will be appreciated that different plant varieties exhibit different phenotypic traits, such as plant height, flowering time, grain size, panicle length and so forth under variable climatic conditions. Generally, determining genetic relationships between different plant varieties and lines assists in predicting genetic merit of each plant variety and line and breeding plants for a specific target area. It is further important to identify plant varieties that exhibit superior genotypes for the specific target area to accelerate the breeding of new plant varieties.

Traditional methods of selecting superior plant varieties for a specific target area are based on phenotype data, genotype data and other available data such as weather and other environmental parameters of the growing conditions in the specific target area. The various weather conditions and other environmental parameters that affect the growth of plants may include temperature, rainfall, humidity, carbon dioxide concentration in air, soil composition, disease pressure for different plant diseases, wind and radiation. Analysing such parameters associated with the target area and selecting plant varieties based on such data is time-consuming, expensive, and prone to inaccuracies when done manually. Furthermore, recent past has witnessed global climatic change resulting in drastic fluctuations in temperature and rainfall and especially an increase in the frequency of extreme events. Methods relying only on testing agronomic performance in field conditions are inaccurate particularly for estimating performance under such extreme conditions, as the full spectrum of environmental conditions are never fully observed in a finite set of field trials performed when selecting variety candidates: while the extreme conditions are likely enough to be met during the commercial lifetime of a variety, the shorter testing period during which variety candidates are selected can pass without the extreme events ever taking place in the trials. Thus, the approach of field testing can fail in efficiently identifying plant varieties that are superior to alternative varieties when considering the full spectrum of field conditions, instead of only comparing variety performance on the set of conditions that occurred in the performed field trials. Especially extreme conditions such as drought, high rainfall, extreme cold/hot and so forth occur rarely enough to not occur in trials. However, they are often enough met during the commercial lifetime.

In addition to the environmental conditions, knowledge about the genetics of plant varieties and origin and/or lineage of plant varieties may be a potential method for selecting the plant variety for the target area. Conventionally, the origin and lineage of plant varieties relies on the available resources including, but not limited to, pedigree charts, phenotype information, breeders' notes and so forth. With the recent advances in technology and prediction models, plant varieties with superior genotype may be determined by employing statistical methods, such as Genomic BLUP (best linear unbiased prediction), whole-genome regression, multivariate methods and the like. Moreover, such methods may be employed for genomic selection (GS) and genome-enabled prediction (GP) models can facilitate selection of superior genotypes and accelerate the breeding cycle. However, even though genomic selection and genome-enabled prediction models offer a potentially advanced alternative to the traditional breeding methods, they do not, to the inventor's knowledge, account for the environmental factors that affect the plant growth in the target area in growing seasons that have not been observed.

Therefore, in light of the foregoing discussion, there exists a need to at least partly overcome the aforementioned drawbacks associated with the selection of a plant variety for cultivation in a target area.

SUMMARY

The present disclosure seeks to provide a method for selecting a plant variety for cultivation in a target area. The present disclosure also seeks to provide a system for selecting a plant variety for cultivation in a target area as well as for selecting a plant line in a breeding program to develop a new variety for a target area. Indeed, the present disclosure seeks to provide a method and system that allow selection of a plant variety for cultivation and/or a plant line for further development, that exploit environmental information but do not require exact environmental information of the target area from the growing seasons from which varieties/lines are selected for. The present disclosure seeks to provide a solution to the existing problem of selecting plant varieties for cultivation and/or breeding for a target area. An aim of the present disclosure is to provide a solution that overcomes at least partially the problems encountered in the prior art, and provides a robust, efficient and easy to implement method for selecting superior plant varieties for cultivation in the target area. Furthermore, it is an aim to provide an approach that enables taking into account variety performance under such conditions under which the varieties/lines have not been tested yet, including the conditions in future growing seasons.

In one aspect, an embodiment of the present disclosure provides a method for selecting a plant variety from a plurality of chosen plant varieties for cultivation in a target area, the plant variety having at least one phenotypic trait, the method comprising:

selecting a selection score function, which selection score function uses as input at least one prediction of one or more phenotypic traits and one or more additional selection score parameters and which selection score function is configured to output a selection score value for a plurality of chosen plant varieties;

estimating values of a first set of one or more environmental parameters for a predefined future period of time for the target area;
receiving
a set of phenotype information comprising phenotypic trait measurements for a first sub-set of a plurality of plant varieties; and
a set of environmental information comprising values of a second set of one or more environmental parameters for said first sub-set;
determining a prediction model for the phenotypic traits, based on the estimated values of the first set of one or more environmental parameters, the received set of phenotype information and the received set of environmental information;
using the prediction model to output predictions for phenotypic traits for the plurality of chosen plant varieties;
using the selection score function to compute selection score values based on the predictions for phenotypic traits for the plurality of chosen plant varieties and one or more additional selection score parameters; and
selecting at least one plant variety to be cultivated in the target area from the plurality of chosen plant varieties, based the computed selection score values of the plurality of chosen plant varieties.

In another aspect, the present description provides a method for selecting a plant line for field trials in a plant breeding program aiming at producing new varieties for the target area, the plant line having at least one phenotypic trait, the method comprising:
selecting a selection score function, which selection score function uses as input at least one prediction of one or more phenotypic traits and one or more additional selection score parameters and which selection score function is configured to output a selection score value for a plurality of chosen plant lines;
estimating values of a first set of one or more environmental parameters for a predefined future period of time for the target area;
receiving
a set of phenotype information comprising phenotypic trait measurements for a first sub-set of a plurality of plant lines; and
a set of environmental information comprising values of a second set of one or more environmental parameters for said first sub-set;
determining a prediction model for the phenotypic traits, based on the estimated values of the first set of one or more environmental parameters, the received set of phenotype information and the received set of environmental information;
using the prediction model to output predictions for phenotypic traits for the plurality of chosen plant lines;
using the selection score function to compute selection score values based on the predictions for phenotypic traits for the plurality of chosen plant lines and one or more additional selection score parameters; and
selecting at least one plant line to be tested in a field trial to develop a new variety for the target area from the plurality of chosen plant lines, based the computed selection score values of the plurality of chosen plant lines.

In still another aspect, an embodiment of the present disclosure provides a system for selecting a plant variety for cultivation in a target area, the system comprising a data processing arrangement configured to:
the plant variety having at least one phenotypic trait, the method comprising:
select a selection score function, which selection score function uses as input at least one prediction of one or more phenotypic traits and one or more additional selection score parameters and which selection score function is configured to output a selection score value for a plurality of chosen plant varieties;
estimate values of a first set of one or more environmental parameters for a predefined future period of time for the target area;
receive
a set of phenotype information comprising phenotypic trait measurements for a first sub-set of a plurality of plant varieties; and
a set of environmental information comprising values of a second set of one or more environmental parameters for said first sub-set;
determine a prediction model for the phenotypic traits, based on the estimated values of the first set of one or more environmental parameters, the received set of phenotype information and the received set of environmental information;
use the prediction model to output predictions for phenotypic traits for the plurality of chosen plant varieties;
use the selection score function to compute selection score values based on the predictions for phenotypic traits for the plurality of chosen plant varieties and one or more additional selection score parameters; and
select at least one plant variety to be cultivated in the target area from the plurality of chosen plant varieties, based the computed selection score values of the plurality of chosen plant varieties.

Embodiments of the present disclosure substantially eliminate or at least partially address the aforementioned problems in the prior art, and provide an efficient, in terms of both cost and time, and accurate plant breeding method.

Additional aspects, advantages, features and objects of the present disclosure would be made apparent from the drawing and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawing. For the purpose of illustrating the present disclosure, exemplary constructions of the disclosure are shown in the drawing. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to FIG. 1, which is a block diagram of a system for selecting a plant variety for cultivation in a target area, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method for selecting a plant variety from a plurality of chosen plant varieties for cultivation in a target area, the plant variety having at least one phenotypic trait, the method comprising:

selecting a selection score function, which selection score function uses as input at least one prediction of one or more phenotypic traits and one or more additional selection score parameters and which selection score function is configured to output a selection score value for a plurality of chosen plant varieties;

estimating values of a first set of one or more environmental parameters for a predefined future period of time for the target area;

receiving
  a set of phenotype information comprising phenotypic trait measurements for a first sub-set of a plurality of plant varieties; and
  a set of environmental information comprising values of a second set of one or more environmental parameters for said first sub-set;

determining a prediction model for the phenotypic traits, based on the estimated values of the first set of one or more environmental parameters, the received set of phenotype information and the received set of environmental information;

using the prediction model to output predictions for phenotypic traits for the plurality of chosen plant varieties;

using the selection score function to compute selection score values based on the predictions for phenotypic traits for the plurality of chosen plant varieties and one or more additional selection score parameters; and selecting at least one plant variety to be cultivated in the target area from the plurality of chosen plant varieties, based the computed selection score values of the plurality of chosen plant varieties.

In another aspect, the present description provides a method for selecting a plant line for field trials in a plant breeding program aiming at producing new varieties for the target area, the plant line having at least one phenotypic trait, the method comprising:

selecting a selection score function, which selection score function uses as input at least one prediction of one or more phenotypic traits and one or more additional selection score parameters and which selection score function is configured to output a selection score value for a plurality of chosen plant lines;

estimating values of a first set of one or more environmental parameters for a predefined future period of time for the target area;

receiving
  a set of phenotype information comprising phenotypic trait measurements for a first sub-set of a plurality of plant lines; and
  a set of environmental information comprising values of a second set of one or more environmental parameters for said first sub-set;

determining a prediction model for the phenotypic traits, based on the estimated values of the first set of one or more environmental parameters, the received set of phenotype information and the received set of environmental information;

using the prediction model to output predictions for phenotypic traits for the plurality of chosen plant lines;

using the selection score function to compute selection score values based on the predictions for phenotypic traits for the plurality of chosen plant lines and one or more additional selection score parameters; and selecting at least one plant line to be tested in a field trial to develop a new variety for the target area from the plurality of chosen plant lines, based the computed selection score values of the plurality of chosen plant lines.

In still another aspect, an embodiment of the present disclosure provides a system for selecting a plant variety for cultivation in a target area, the system comprising a data processing arrangement configured to:
the plant variety having at least one phenotypic trait, the method comprising:

select a selection score function, which selection score function uses as input at least one prediction of one or more phenotypic traits and one or more additional selection score parameters and which selection score function is configured to output a selection score value for a plurality of chosen plant varieties;

estimate values of a first set of one or more environmental parameters for a predefined future period of time for the target area;

receive
  a set of phenotype information comprising phenotypic trait measurements for a first sub-set of a plurality of plant varieties; and
  a set of environmental information comprising values of a second set of one or more environmental parameters for said first sub-set;

determine a prediction model for the phenotypic traits, based on the estimated values of the first set of one or more environmental parameters, the received set of phenotype information and the received set of environmental information;

use the prediction model to output predictions for phenotypic traits for the plurality of chosen plant varieties;

use the selection score function to compute selection score values based on the predictions for phenotypic traits for the plurality of chosen plant varieties and one or more additional selection score parameters; and select at least one plant variety to be cultivated in the target area from the plurality of chosen plant varieties, based the computed selection score values of the plurality of chosen plant varieties.

The present disclosure thus provides a method and a system for selecting a plant variety for cultivation in a target area as well as a method and a system for selecting a plant line for field trials in a plant breeding program aiming at producing new varieties for the target area.

The background of the present disclosure is that the phenotypic traits of different plant varieties are different and the phenotypic traits may depend on the environment in which the plants are grown in. Depending on the environmental conditions, different plant varieties and agronomic practices provide optimal yields and revenues. Many phenotypic traits, such as yield, protein content and similar have a significant impact on the commercial successfulness of the practice of agriculture. Selecting plant varieties that are most likely to be optimal in terms of phenotypes such as yield and quality in the growing conditions at hand improves the success of agriculture. Plant breeding, on the other hand, aims at developing new varieties that perform as well as possible in the target area of the breeding program. During the breeding program, identifying lines that are likely to become new varieties with improved performance in the target area should preferably be identified as early as possible. In this disclosure in the context of plant breeding, the target area corresponds to the target population of environments (TPE) term used in the plant breeding literature. The present disclosure also addresses this need.

Furthermore, it will be appreciated that the approach presented by the embodiment can take into account extreme weather conditions, which may not occur during a given test trial. However, the present method will also be beneficial for estimating the impact of less extreme weather conditions.

Beneficially, for example the present disclosure is efficient in analysing environmental parameters at a micro level such as of the target area. Consequently, the present disclosure provides a method for extracting an adequate amount of information about the target area and applying the micro-environment data for selecting plants pertaining suitable characteristics thereto for cultivation in the target area. Based on such cultivation methods, benefits such as lower rate of crop failure, high yielding crops, better rotation of crops, and the like can be obtained Notably, a vast range of plant varieties can be developed and cultivated efficiently based on the environmental parameters of the target area. It is furthermore possible to develop and optimise a new plant variety for a given target area, the optimisation depending on the wishes of the plant breeder which are formulated as the selection score. Indeed, the plant variety may be optimised for example for yield, protein content, fast growth etc. as well as combinations of these.

It is especially to be noted that all embodiments, details and variations listed in this description in connection with the method for selecting a plant variety for cultivation in a target area apply mutatis mutandis to the method for selecting a plant line or a variety candidate for field trials in a plant breeding program aiming at producing new varieties for the target area, with the proviso that "plant variety" is replaced with "plant line" and "variety candidate". Similarly, all embodiments, details and variations disclosed in connection with the methods apply to the system and vice versa.

In the present disclosure, the term "plant variety" relates to a group of plants within the same botanical taxon of the lowest grade known (namely a species). Moreover, the expression of characteristics can be used to distinguish the plant variety from any other group of plants (within same and/or different species). For example, rice of different varieties may exhibit different characteristics like grain size, colour, texture and the like.

In the present disclosure, the plant variety is selected from a plurality of chosen plant varieties, the plurality of chosen plant varieties being the set of varieties from which one or more varieties will be selected from. One or more varieties may be selected. When selecting plant varieties, they can be selected from one or several species. Indeed, when describing selection from a set of plant varieties, the set may include varieties of different plant taxa. For example, the set of varieties to select from may comprise one or more varieties from the plant species of barley, wheat and fava bean. In the plant breeding context, the lines are naturally from the same plant taxa.

Throughout the present disclosure, the term "target area" relates to a location where plants are grown and where products in the form of plants or plant parts are produced for harvest, i.e. an area where the selected varieties should perform according to breeder or the farmer. The size of the target area can range from very small to very large and is generally expressed in square meters or acres of land. The target area can be an in an open field or in a greenhouse. For example, the target area may be a country, a field parcel, a trial plot used in a plant breeding program or a pot in a laboratory experiment. Optionally, the target area can be geographical region constituted by one or more sub-areas, i.e. the one or more sub-areas constitute the target area.

In the present description, by "future period of time" it is meant any period of time desired. It is naturally possible to use the present method also to past times, if so wished. Optionally, the predefined future period of time corresponds to at least one growing season for the one or more chosen plant varieties. For example, a plant variety may grow throughout the year or only a few months of the year. Therefore, the predefined future period of time may be for example 1, 2, 3, 4, 5, 6, 7, 8, 9, 10, 11 or 12 months. The predefined future period of time may also correspond to more than one growing season, such as two, three, four, five, six or more growing seasons. A growing season may be one summer or one year, for example. Optionally, the predefined future period of time corresponds to at least one growing season for a plant variety. For example, a plant variety may grow throughout the year or only a few months of the year. Therefore, the predefined future period of time may be for example 1, 2, 3, 4, 5, 6, 7, 8, 9, 10, 11 or 12 months. The predefined future period of time may also correspond to more than one growing season, such as two, three, four, five, six or more growing seasons. A growing season may be one summer or one year, for example. It will be appreciated that predefined future period of time can be preprogrammed into the computer programs and/or routines configured to estimate one or more environmental parameters.

By "phenotypic trait" in the present disclosure, it is meant observable plant traits such as yield, yield components, root traits, height, thousand grain weight, hectolitre weight, protein content, nutrient concentrations, growing time in growing degree days to reach a certain developmental stage, morphological structure, disease tolerance and also laboratory measurements such as gene expression and metabolomics measurements, and also indexes computed from some measurements such as leaf area index (LAI). According to an embodiment, the phenotypic traits of the plant variety correspond to at least one of yield, yield components, root traits, quality traits such as protein content and taste, growth speed and sensitivity to diseases of the plant variety By "phenotype information", it is meant measurements of observable traits similar to the ones of listed above. In the present disclosure, the phenotype information is obtained from a set of experiments, whose environmental conditions are measured as the values of the second set of environmental parameters and stored as the values of the second set of one or more environmental parameters. The experiments can be field trials or greenhouse trials or trials performed in a laboratory. The second set of environmental parameters can be the same as in the first set of environmental parameters, or they can be different, as will be discussed in more detail below. When the first set of one or more environmental parameters is different from the second set of one or more environmental parameters are different, the first and second sets of environmental parameters need to be related so that the values of the first set of one or more environmental parameters can be predicted from the values of the second set of one or more environmental parameters. For example, machine learning can be used for converting the values of the two sets of parameters, possibly by using some data set that connects these two sets of environmental parameters together.

Throughout the present disclosure, the term "genotype" relates to a genetic constitution of a plant variety and any variations thereof. Optionally, the genotype information comprises genealogy of the plant variety. The term 'genealogy' relates to a study of origin and lineage of an organism, such as a plant variety. Specifically, genealogy determines connection of one generation to the next based on evidences extracted from valid sources. More specifically, genealogy uses available records and/or genetic analysis to demonstrate the relationship between two or more generations. Moreover, available records may be selected from traditional knowledge, plant breeders' analysis, pedigree charts and/or family group sheets for plant varieties and the like for drawing connections of a plant variety with its related varieties and/or ancestors. Furthermore, genetic analysis is a superior alternative to the conventional methods for deducing lineage of a plant variety. Specifically, genetic analysis employs a DNA test of two or more plant varieties to find a probable relationship with a relatively recent common ancestor. It will be appreciated that the DNA test ensures establishing relation between distant relatives from different branches of the family because DNA is inherited by future progeny from one of a maternal, paternal or both parents without substantial mutations.

Optionally, the genotype information comprises at least one of genealogy of the plant variety, Single Nucleotide Polymorphism (SNP) measurements of the plant variety, sequencing measurements of the plant variety and epigenetic measurements of the plant variety. The term "Single Nucleotide Polymorphism" (SNP) relates to genetic variations at a single nucleotide in the genome. SNPs can be found present in non-coding regions of genes, in the intergenic regions or in coding regions of genes. Specifically, measuring SNPs and the associated phenotypes enables deducing genetic information about a plant variety with a good coverage.

Optionally, the genotype information comprises sequencing measurements of the plant variety and epigenetic measurements of the plant variety. Apart from genetic mutations, external or environmental factors contribute to heritable changes in the genes without altering the DNA sequence of the plant variety and heritable changes of this like can be measured as epigenetic measurements. Furthermore, de novo sequencing with the next-generation sequencing technology allows for studying the genotypic and phenotypic alterations in a plant variety. Specifically, epigenetic and sequencing measurements of the plant variety enables deciphering the overall genotypic information of the plant variety. Genotyping can be carried out according to any known method, or genotype information may be obtained from an existing source of information such as a data bank. Moreover, changes in genotype may be incorporated into measurements of phenotype when both genotype information and phenotype information are used.

Throughout the present disclosure, the term "environmental parameters" relates to one or more measurable factor, forming one of a set, that defines conditions relating to the natural environment. Specifically, the environmental parameters provide information related to conditions surrounding and within the target area. Optionally, the environmental parameters include information that describes the physical, chemical or biological factors associated to the natural environment of the target area. For example, the information describing the environmental parameters may include the data records related to the amount of organic matter contents in the soil of the target area that affects the cation exchange capacity and the capacity for buffering changes in soil pH. It is also to be noted that the environmental parameters of the first set and of the second set may be the same parameters or they may be different (partially or fully). For example, a first set may consist of rain and temperature, while a second set may consist of rain and wind. The sets are however selected from the same list of environmental parameters.

These parameters can be measured with varying accuracies. For example, it is possible to measure one parameter with the accuracy of one measurement per square kilometre while measuring another parameter with accuracy of one measurement per square metre. Soil moisture and/or soil temperature can be measured at various depths, such as at the surface, at 1 cm depth, at 5 cm depth, at 30 cm depth and at 1 m depth. All soil parameters (comprising and not limited to moisture, temperature, composition, nutrients) can be at different vertical resolutions. For example, one measurement can be made for a geographic region of tens of square kilometres or several measurements can be made for one individual field parcel. Still further, the environmental parameters can be measured with varying frequencies, such as once per minute, once per hour, once per 6 hours, once per day or once per week or month. It is to be understood that when more than one environmental parameter is used, the above parameters can be freely combined as well as their measurement accuracy and frequency.

Optionally, the one or more environmental parameters of the first set of one or more environmental parameters and the second set of one or more environmental parameters comprise one or more of temperature, rain fall, air humidity, carbon dioxide content, soil composition, soil moisture from at least one depth, soil temperature from at least one depth, soil nutrient concentrations, disease pressures of different plant diseases, wind velocity, wind variability, radiation intensity and radiation spectrum.

For example, the data processing arrangement may consider data describing the temperature, rain fall, air humidity, carbon dioxide content, soil composition, soil moisture, soil nutrient concentrations, plant diseases, wind velocity, wind variability, and radiation intensity and spectrum of an area (namely the target area) as parameters that describe the natural environment of the target area. In such example, the data may describe time series and variations in temperature, rain fall, air humidity, carbon dioxide content, soil composition, soil moisture, soil nutrient concentrations, wind velocity, wind variability, and radiation intensity and spectrum. Furthermore, the environmental data can be obtained at different spatial and temporal resolutions. Furthermore, the data may describe information related to different plant disease pressures that affects the plants in the target area.

Optionally, the environmental parameters include information of the previous growing seasons from the environment. For example, data from crop rotation consisting of records of the crop species and varieties used in the previous growing seasons, the yields obtained during the previous growing seasons, environmental information related to the conditions from which the yield data from the previous seasons were obtained from.

Optionally, the environmental parameters include information about crop management, such as fertilizer use, herbicide use and pesticide use. For example, crop management data can consist of the timing of the operations, information about the chemicals used, the quantities of chemicals used, nutrient concentrations in the fertilizers.

According to an embodiment, the values of the one or more environmental parameters of the first set of environmental parameters are estimated based on at least one of historical data related to weather conditions and other environmental parameters associated with the target area, a user-defined simulation, a climate simulation associated with the target area and weather forecast associated with the target area.

Optionally, the values of the one or more environmental parameters measured at a high spatial and/or temporal resolution can be combined for decision making for larger areas by computing statistics of the environmental data for the larger area directly or by computing predictions at a finer resolution and the combining the predictions for the larger area.

The present method can be used for predicting the influence of weekly, daily or hourly values of the environmental parameters during the growing season. Indeed, the environmental parameters vary significantly during one growing season, and the impact of the variations to the development of the plant differs, depending on the stage of growth of the plant. Thus, it may be useful to be able to predict daily environmental parameters during the growing season, and this can be achieved also by the present method and system. An example of using environmental parameters that are measured daily, hourly or weekly in the method is to output the selection score values with the environmental parameter values from the growing seasons from the earlier 10 years. To clarify, this will give 10 different selection score values for each of the varieties and varieties can then be compared in terms of these 10 selection score values for example by comparing average selection score values over the 10 growing seasons. It will be appreciated that the length of the growing season may differ between different years and transformations that process the time series of different lengths to the same mathematical space can be used to make the time series from different growing seasons comparable a processable with machine learning algorithms.

According to an embodiment, the selection score function is based on the prediction for one or more phenotypic traits from the prediction model and further comprises an agronomic optimisation objective function for processing one or more phenotypic trait predictions and optionally a set of other parameters for the agronomic optimisation objective function; and a probability distribution associated with the other parameters of the agronomic optimisation objective function.

The selection score function thus takes as input one or more phenotypic trait predictions for the target area for the predefined future period of time for each of the varieties from the plurality of chosen varieties. The phenotypic trait predictions are obtained as the output of a prediction model for the phenotypic traits. The predictions of the prediction model for the phenotypic traits can also comprise a probability distribution for the predicted value to quantify the probabilities related to different predicted outcomes. When the estimate for the values of the first set of one or more environmental parameters is a probability distribution, the probability distribution can be integrated over to obtain a probability distribution for the phenotypic trait predictions.

Different selection score functions can be built to address different objectives. The selection score function may optionally comprise an agronomic optimisation objective function. The selection score function outputs selection score values based on phenotypic trait predictions. The agronomic optimisation objective function is a mathematical function used within the selection score function to process the predictions for one or more phenotypic traits. The agronomic optimisation objective function may further have other parameters that are required as input when the agronomic optimisation objective function is used.

For example, different quality traits that affect the sales price can be used as terms in the agronomic optimisation objective function which is a mathematical formula that takes into account, for example, the breeders or farmers knowledge of how revenue is created from agronomic produce as a function of the different quality traits. By building such a selection score, the selected line/variety directly aims to maximise revenue rather than only yield or quality.

An example is thus constructing a selection score function to create an approximation for the expected revenue obtained from selling the harvest resulting from cultivating a selected variety. To provide the approximation for the aforementioned objective of the farmer, the agronomic optimisation objective function could process, in an example, the expected yield and the expected price obtained by selling the harvested crop. The expected sales price is an example of the other parameters of the agronomic optimisation objective function and additionally, probability distributions for such parameters can be taken into account in the agronomic optimisation objective function. In the example where the selection score function mimics the expected revenue obtained from selling the harvest, the varieties with high selection score function values are preferred to varieties with low selection score function values.

Optionally, the other parameters of the agronomic optimisation objective function may have associated probability distributions and the selection score function can process these optional probability distributions for other parameters of the agronomic optimisation objective function. Summary statistics of the probability distributions associated with the other parameters of the agronomic optimisation objective function such as the mean, median and quantiles can be used in the agronomic optimisation objective function. Optionally, the probability distributions associated with the other parameters of the cost function for agronomic optimisation may be processed in the selection score function by integrating the value of the selection score over the probability distributions of the other parameters of the agronomic optimisation objective function.

In an example, where a selection score function is constructed that mimics the revenue obtained from cultivating a variety, the agronomic optimisation objective function is defined as a mathematical equation for revenue that takes into account, for example, yield, one or more phenotypic traits that are related to quality and the sales price obtained at different quality levels of the produced grain. In this example, the other parameters of the cost function for agronomic optimisation is the sales price obtained at different quality levels of the produced grain and a probability distribution is assigned for the sales price obtained at different quality levels of the produced grain by processing external data. Then the cost function for agronomic optimisation is integrated over the joint probability distribution of yield, the phenotypic traits associated with quality and the sales price obtained at different quality levels of the produced grain parameter, to obtain the expected revenue.

Selection is based on comparing the selection score function values for the different varieties of the plurality of chosen plant varieties in the target area in a predefined future period of time. The varieties for which the values of the selection score function are desirable are selected as more preferable when compared with varieties for which the values of the selection score function are undesired. According to an embodiment, the selected plant variety is one from the one or more chosen plant varieties with the highest value of the selection score.

For a given target area, the method thus comprises computing the selection score values for a set of varieties using the environmental parameter values for a given time period, for example the preceding 30 years in that target area. Thereafter, the method determines which plant variety would have achieved for example the highest average selection score over these 30 years. For example, it is determined which plant variety has the highest average predicted yield or highest average predicted protein content in the conditions that have been seen in the target area during the past 30 years.

Optionally, according to an embodiment, the method comprises receiving genotype information of one or more of the plant varieties of the plurality of plant varieties and using the genotype information in the prediction model for the phenotypic traits. Genotype information can thus be used as an additional variable in the determination the predictions of the phenotypic traits. In the following, when genotype information is indicated in this connection, it is to be understood to be an optional feature, even if not necessarily mentioned.

According to an embodiment, the prediction model comprises
- a variety specific main effect prediction model, configured to predict the effect of each plant variety on phenotypic traits by processing the received set of phenotype information and optionally the received environmental information and optionally the received genotype information;
- a genotype-environment interaction model, configured to predict differences between phenotypic traits of plant varieties of the plurality of chosen plant varieties in relation to the first set of environmental parameters by processing the received set of phenotype information and the received set of environmental information and optionally the received genotype information and the values of the first set of environmental parameters; and
- an environment-specific effect prediction model configured to predict the effect of each environment on the phenotypic traits by processing the received phenotype information and optionally the received genotype information and optionally the received environmental information and the values of the first set of environmental parameters.

The prediction model for the phenotypic traits can provide a probability distribution for the predicted outcomes and this probability distribution can be processed in the selection score function. In an example, the selection score function can be the expected yield, which is obtained by integrating yield over its probability distribution. In another example, the breeder may aim for a high guaranteed yield (i.e. a yield that is guaranteed even in not ideal environmental conditions). In the case of the high guaranteed yield, the selection score function to be maximised in variety selection can be a low quantile such as the 25th percentile of the yield distribution.

The predictions are based on a first set of one or more environmental parameters, whose values are estimated for the target area for the predefined future period of time. Optionally, a probability distribution may be estimated for the values of the first set of environmental parameters and the probability distribution can be processed by the prediction function. An example of the first set of environmental parameters are daily temperature values in the target area during the next growing season. The predictions of the phenotypic traits of the prediction model are based on processing a set of phenotype information comprising phenotypic trait measurements for a first sub-set of a plurality of plant varieties and a set of environmental information comprising values of a second set of one or more environmental parameters for said sub-set and optionally genotype information. The set of environmental information consists of values of the second set of one or more environmental parameters recorded from a set of experiments, from which set of experiments the set of phenotype information is obtained from. Optionally, the phenotype information may not be available for the plurality of chosen plant varieties, in which case it is a second sub-set of the plurality of plant varieties and distinct from the first sub-set of the plurality of plant varieties for which first sub-set phenotype information is available in the set of phenotype information and for which sub-set the associated environmental information is available in the set of environmental information. In the case when phenotype information is not available for the plurality of chosen plant varieties, in order to propagate information about the variety specific responses to environmental conditions, environmental conditions which are represented in the prediction model as the values of the first set of one or more environmental parameters, genotype information for the for the plurality of chosen plant varieties is needed and genotype information is needed for the first sub-set of the plurality of plant varieties for which phenotype information and the associated environmental information are available. Optionally, the plurality of chosen plant varieties may be a part of the first sub-set of the plurality of plant varieties for which the phenotype information and environmental information are available. In this case, variety specific responses to the first set of one or more environmental parameters may be predicted also without genotype information. In this case, genotype information can still be processed in the prediction model in addition to the set of phenotype information and the set of environmental information.

The prediction model may be for example generated by implementing machine learning algorithms and the values of the first set of environmental parameters are estimated by using historical data from the target area as samples of the values of the first set of environmental parameters.

The method thus comprises determining a selection score value of the each of the plurality of chosen plant varieties from the phenotypic trait predictions in the target area, which phenotypic trait predictions are based on the estimated values of the first set of one or more environmental parameters, the received set of phenotype information and the received set of environmental information and the optionally the received genotype information. The method may also comprise using a probability distribution of the one or more environmental parameters, as discussed above. Herein, the selection score value of a particular plant variety may correspond to quality as well as quantity of the produce obtained by cultivation of that plant variety. Further, the selection score of a particular plant variety may correspond to minimizing the variance in the quality and quantity of the produce obtained by cultivation of that plant variety. Specifically, the method processes the estimated values of the first set of one or more environmental parameters related to the target area, the received set of phenotype information, the received set of environmental information and the optionally received genotype information of each of the plurality of chosen plant varieties, and subsequently determines phenotypic trait predictions used for processing the selection score values of the each of the plurality of chosen plant varieties in the target area. For example, the method processes the estimated values of the first set of one or more environmental parameters of the target area and the optionally received genotype information of each of the plurality of chosen plant varieties and phenotype information obtained for the plurality of chosen plant varieties that were grown under environmental conditions, which have been measured in terms of a second set of environmental parameters and the data comprising the measured values of the second set of environmental parameters is available.

In an example, the analysis enables determination of the reaction of the genotypes of the plurality of chosen plant varieties when subjected to the probability distribution of conditions in the target area described as an estimated probability distribution of the first set of one or more environmental parameters of the target area. Subsequently, the probability distribution of the selection scores in the target area are determined for the plurality of chosen plant varieties based on the estimated distribution of the first set of one or more environmental parameters.

The method may optionally use a prediction model that comprises a genotype-environment (also sometimes referred to as "GxE") interaction model wherein the genotype-environment interaction model predicts the differences of a phenotypic trait between varieties in the target area in relation to the first set of environmental parameters. To clarify, different varieties respond in a different way to their growing environment and these differences are predicted by the genotype-environment interaction model. In this embodiment, the differences between the plant varieties of the plurality of chosen plant varieties are predicted in the target area in the predefined future period of time in relation to the first set of one or more environmental parameters by processing the received set of phenotype information, the received set of environmental information and the optionally received set of genotype information in the genotype-environment interaction model. Moreover, in this example, the phenotypic trait predictions used in the selection score function are affected by the predictions of the genotype-environment model. The interaction model refers to a description of a way for implementing the software interaction function with a combination of the interaction elements, and the interaction element refers to a functional element for interacting information with the actual software modelling environment. Specifically, the genotype-environment interaction model predicts differences between the phenotypic traits of different plant varieties in relation to the same estimated values of the first set of one or more environmental parameters by processing the received phenotype information and the received set of environmental information and optionally the received genotype information as the interaction elements. Furthermore, the genotype-environment interaction model can include one or more layers of latent variables in a probabilistic model architecture through which the interaction effects are modelled and this structure is used as a template in the actual software modelling environment to be configured to form the software interaction models. It will be appreciated that, the genotype-environment interaction model may refer to a hardware component or logic (computer program). Therefore, the module not only refer to a computer program module, but also refer to the hardware configuration of the module. Optionally, genotype-environment interaction model may correspond to a function, namely, that partly determines the selection score value of each of the plurality of chosen plant varieties in the target area in relation to the values of the first set of one or more environmental parameters. Optionally, in an implementation, genotype-environment interaction model can include a program, or may be composed of a plurality of program modules, and in turn, a module may be composed of a plurality of programs. Further, the plurality of modules may be executed by a single computational entity and a single module may be executed by a distributed environment or in parallel environment multiple computational entity.

Optionally, the prediction model comprises information about phenotypic trait values of different plant varieties in relation to the first set of environmental parameters. Optionally, the information about phenotypic traits of different plant varieties in relation to different environmental parameters can be fetched from the third-party service provider. In an example, the third-party service provider may be online database service that is operable to curate the set of phenotype information and the set of phenotype information and the optional set of genotype information about different plant varieties in relation to different environmental parameters into phenotypic trait predictions, which phenotypic trait predictions can be predicted values of probability distributions thereof. In such example, the database arrangement is operable to fetch the phenotypic trait predictions for different plant varieties in relation to different environmental parameters from the online database service. Furthermore, the fetched phenotypic trait predictions about different plant varieties may be used by the genotype-environment interaction model to perform further computation process.

Optionally, the prediction model can be implemented to generate samples from the probability distribution of phenotypic traits for each the plurality of chosen plant varieties and is operable to consider the weather observation data of the target area for a past time period that is assumed to be predictive of the environmental conditions during the predefined future period of time for which the samples from the probability distribution of phenotypic traits are to be determined. For example, to produce samples from the probability distribution of phenotypic traits for each the plurality of chosen plant varieties in the target area for future period of time, such as two years, the prediction model may consider the weather observation data of the target area for past two years or the past five years.

Optionally, the prediction model can generate plurality of samples from the predicted probability distribution of phenotypic traits associated with the target area for each the plurality of chosen plant varieties. Based on the plurality of samples from the probability distribution of the phenotypic traits of each the plurality of chosen plant varieties, a corresponding sample of the probability distribution of the optional cost function for agronomic optimisation is obtained and the value of the selection score function value is can be obtained by processing this sample. In an example, a plurality of samples from the predicted probability distribution for the phenotypic trait yield is obtained by processing the environmental parameters comprising of weather measurement time series and soil information from the previous ten growing seasons. For each of the previous ten growing seasons, the prediction model is used to process the environmental information from each of the previous growing seasons into a yield prediction for each of the plurality of chosen plant varieties, giving a sample consisting of ten values from an assumed probability distribution for yield in the target environment for each of the plurality of chosen plant varieties. Each of these samples can then be used as input in a cost function for agronomic optimisation giving ten samples from an assumed probability distribution for the agronomic optimisation objective function for each variety of the plurality of chosen plant varieties. The selection score function can then process these samples for example by taking the mean.

Optionally, the data processing arrangement is configured to generate the prediction model by implementing machine learning algorithms and using historical data related to first set of one or more environmental parameters affecting growth of plant varieties with different genotypes to generate a sample from the probability distribution of the growing conditions to be used for phenotypic trait prediction, the sample from the probability distribution of the growing conditions being approximated as the measured values of the first set of environmental parameters in the historical data.

Herein, the machine learning algorithms relate to software-based algorithms that are executable upon the computational entity and are operable to adapt and adjust their operating parameters in an adaptive manner depending upon information (namely, received set of environmental information, the received set of phenotype information and the optionally received genotype information) that is presented to the software-based algorithms when executed upon the computational entity. Optionally, the machine learning algorithms involve a decision tree or network defining decision states concerning whether or not a particular environmental parameter has an interaction effect with a genotype information. Optionally, the learnt dependencies are aggregated across each of the plurality of chosen plant varieties in the target area.

The prediction model can thus be implemented, for example, by using machine learning methods. Examples of machine learning techniques which can be used in implementing the prediction model include Bayesian modelling, probabilistic latent variable models, matrix factorization methods, deep learning methods, kernel methods and multiple kernel learning. The techniques used for learning the values of the machine learning model parameters are not discussed in this disclosure.

Optionally, the phenotypic trait prediction is determined by processing the estimated values of the first set of one or more environmental parameters, the received set of environmental information and the received set of phenotype information and the optionally received genotype information in the prediction model. Optionally, the phenotypic trait prediction is a numerical value that can be determined by the prediction model. The prediction model is operable to determine the phenotypic trait prediction for each of the plurality of chosen plant varieties in the target area.

The prediction model may comprise at least one of a variety specific main effect prediction model that predicts the effect of each plant variety on phenotypic traits by processing the received set of phenotype information and optionally the received set of environmental information. When genotype information is also used, it is used in this processing, too. Furthermore, a genotype-environment interaction model may be used wherein the genotype-environment interaction model predicts differences between phenotypic traits of plant varieties of the plurality of chosen plant varieties in relation to the first set of environmental parameters by processing the received set of phenotype information and the received set of environmental information and the optionally received genotype information and the values of the first set of environmental parameters.

Optionally, the prediction model may predict the environment-specific main effect, which is the effect of the growing environment on all the plant varieties grown therein based on the first set of environmental parameters.

Optionally, the prediction model can predict the variety specific main effects, the genotype-environment interactions and the optional environmental main effects without an explicit division of prediction model parameters into variety specific main effects, the genotype-environment interactions and the environmental main effects.

According to an embodiment, a variety is considered superior to another variety in a target area, when the selection score value of the variety is preferable as compared with the selection score value of another variety. For example, the selection score function can be the expected value, median or a lower quantile of the probability distribution of the phenotypic trait generated by the prediction model. For example, the selected plant variety may be at least one from plurality of chosen plant varieties with the highest determined expected for yield, yield which has a probability distribution given by the prediction model. Preferable values may be as small or as large values as possible. For example, when the selection score function is built for lodging susceptibility such as the expected value of lodged field area, a value close to zero is preferable to a large value. For example, when the selection score function is built for yield, a large expected value over the probability distribution of the phenotypic trait is preferred as compared to a small value. The agronomic optimisation objective function can take into account the predictions for one or more phenotypic traits, as discussed above. Optionally, the agronomic optimisation objective function may, for example, give the predicted values for several phenotypic traits either equally or differentially weights, depending on the desired end result. Optionally, the agronomic optimisation objective function may comprise more complex functional relationships between the different phenotypic traits.

Optionally, the selection score of the plant variety corresponds to the predicted yield of the plant variety over the predefined future period of time. Specifically, the selection score of the at least one plant variety is associated with the yield of the plant variety over a predefined duration of time required by the plant to grow completely. Optionally, the selection score of the plant variety may be associated with the size of the fruit, size of the flower, ripening of the fruit, and so forth.

Optionally, the performance of each one of the plant varieties to the estimated one or more environmental parameters is identified, and the most suitable at least one of the plant variety is selected to be cultivated in the target area. In the present examples, plant variety may be selected based on the historical data available for its well-suited growth in a particular growth condition. Specifically, the growth conditions are values of various environmental parameters obtained from the historical data from the previous growing seasons. Optionally, the growth conditions are values of various environmental parameters obtained from a few weeks before sowing the plant until the harvest in the previous season. It will be appreciated that the growth conditions vary from one year to another during the growing season. Also, a permanent growth condition, such as soil composition, that remains almost unchanged from year to year, may be chosen to determine the plant variety that could be cultivated in the target area. For example, an arid area, such as a desert is suitable for growing of different varieties of cactus, however, such environment would not favour growth of one or more varieties of mango tree. In an example, the selection score of mango as compared with the selection score of cactus is higher when using the system to compare growing the mango and the cactus in conditions that are optimal for mango. However, mango plant may tolerate dry conditions, waterlogging and moderately saline soil, nevertheless, the selection score of mango plant grown under the latter environmental parameters is not high as compared with plants that are well adapted to such conditions, such as the cactus. Optionally, the historical data, related to one or more environmental parameters affecting growth of each the plurality of chosen plant varieties with different genotypes, may include weather history information of the target area. For example, the weather history information may include the weather observation data from previous years or weather predictions/simulation data at the target area. Furthermore, the weather history information may be used by the prediction model to calculate a probability distribution of phenotypic traits that are used to determine the selection score for each the plurality of chosen plant varieties for predefined future period of time.

In an embodiment, one or more prediction models may be employed to select the one or more plant varieties with a potentially high selection score value, or for predicting multiple phenotypic traits of the plant or in the estimated one or more environmental parameters. Optionally, the selected plant variety is at least one from the one or more chosen plant varieties with the most desired selection score function values. The plant varieties with the highest selection score are selected for cultivation in the target area. Optionally, different plant varieties varying in their selection score in ranges near the highest plant selection scores may also be selected to be grown along with the plant varieties exhibiting highest plant selection score.

Optionally, at least one plant variety may be selected based on the selection score function values computed for the different plant varieties. In an example, expected yield of each the plurality of chosen plant varieties may be determined by the prediction model hosted in the data processing arrangement. In such example, based on the plant variety having the highest expected yield among the plurality of chosen plant varieties may be selected as the at least one plant variety to be cultivated in the target area.

Optionally, the target area for which the at least one plant variety needs to be selected can be divided into a plurality of sub-areas. Subsequently, the selection score function value of each of the plurality of plant variety with respect to the environmental parameters associated to each of the plurality of sub-areas in the target area is determined. Furthermore, at least one plant variety to be cultivated in each sub-region of the plurality of sub-regions of the target area based on the determined selection score values associated therein is determined.

Optionally, in the event wherein the target area is a large area, the growing habitats within the plurality of portions of the target area may be determined. Furthermore, the distribution of growth conditions of each of the plurality of portions of the target area can be combined to the distribution of growth conditions of the entire target area. For example, for a specific oat genotypes (lines) produced in the plant breeding process for further experiments to create a new variety of oats for a target area (namely 'A'), it is possible to calculate for each of the portion of the target area 'A' that cultivate oats, distribution of growth conditions or samples thereof (such as growth conditions in the target area 'A' used for oat cultivation in the last 20 years). Furthermore, field-specific growth condition samples (1 year=1 sample) are weighed by the sizes of the fields as a portion of the size of the target area 'A', which results in the distribution of growth conditions. In such example, a variety of oats can be selected for further research which, according to the prediction model, will produce the most desirable yield distribution in the growing environment of the target area A. Furthermore, in such example, it is also possible to calculate the field size weighted forecasts of crop yields for each oats line for the past twenty years and select those lines for further development that according to the prediction model may have the best average yield.

To summarise, the data processing arrangement is configured to select at least one plant variety to be cultivated in the target area based on the selection score value of the at least one plant variety in the target area. Specifically, the one or more computer programs models and/or routines hosted in the data processing arrangement is operable to select at least one plant variety to be cultivated in the target area based on the selection score of the at least one plant variety in the target area. Optionally, the one or more computer programs models and/or routines is operable to compare the selection score values of the each of the plurality of chosen plant varieties to determine at least one plant variety to be cultivated in the target area. In an example, the plurality of chosen plant varieties may be A1, A2, A3, A4 and A5, and the corresponding selection score values associated may be B1, B2, B3, B4 and B5. Further, in such example, the numerical value of B1 is greater than the B2, the numerical value of B2 is greater than the B3, the numerical value of B3 is greater than the B4, and the numerical value of B4 is greater than the B5. Moreover, in such example, the one or more computer programs models and/or routines may be operable to compare the selection score values associated with B1, B2, B3, B4 and B5, and subsequently identify the at least one plant variety having the maximum selection score value, namely B1 in the present example. Therefore, in such example, the one or more computer programs models and/or routines may be operable to select at least one plant variety, namely A1 to be cultivated in the target area.

The system and method of the present disclosure can be implemented for predicting yields and other phenotypic traits of plant varieties in new environments before the environmental information of the said plant variety for the future predefined period of time is available. The present system and method may also provide an approach for accounting also for G×E effects which does not specifically need accurate information from the growth season. In an experimental setup for the present system, the prediction accuracy of modelling variety specific main effects and genotype-environment interactions was investigated. The performance of model $M^{hist}_{G+E+GE}$ which used historical weather data to estimate some of the values of the first set of one or more environmental parameters was investigated and compared with non-realistic ideal situation having in-season data ($M_{G+E+GE}$) and a model without the G×E interaction ($M_{G+E}$) It was found that the approaches including G×E interaction, $M_{G+E+GE}$ and $M^{hist}_{G+E+GE}$ had higher prediction accuracy than the industry standard. Importantly, the performance gain was achieved also when using historical weather observations and not only with accurate in-season data. Further, it was found that by increasing model complexity by adding more G×E components, the performance of the model consistently improved, which highlights the potential to increase accuracy through complex modelling of G×E. Evidence of working of this embodiment has been disclosed in the article cited below.

The results of the techniques implemented in the present system indicate that improvements in yields could be achieved by dividing current large target populations of environments (TPE) into several smaller parts. Furthermore, the methodology presented in this embodiment can be used to prevent overfitting to the conditions which took place in the field trials performed during the breeding process of a new variety when developing only one variety for an existing large TPE, as in traditional breeding.

Optionally, to prevent overfitting to the conditions which took place in the field trials performed during the breeding process of a new variety, a selection score function can be implemented for breeding to address the conditions in the TPE directly by using information about the fields in the TPE. As for the notation, the plurality of chosen plant varieties consists of G varieties and the varieties are indexed with $g \in 1, \ldots, G$. Traditional breeding often makes the implicit assumption that the obtained yield and other phenotypic trait measurements in the field trials in the plant breeding program are representative of variety candidates' performance in the conditions of the full TPE. In an example, yield measurements have been obtained in a breeding program in E field trials for each variety g, which field trials are indexed with $e \in 1, \ldots, E$. In the example, the plant breeder considers each of the E experiments equally representative of the TPE, in which case the estimate for the variety candidate specific yield distribution in the TPE is obtained as $$p(yield_g \mid TPE) \approx \frac{1}{E}\Sigma_e p(yield_g \mid environment_e) \qquad (1)$$

where the term $p(yield_g|environment_e)$ is the variety candidate specific probability distributions for yield estimated for each of the E field trials. One problem with this approach of the example is that the results (obtained yield measurements) from the different field trials may not be equally representative of the TPE and manually weighting the results is error prone. The method and system in this embodiment can be used to estimate a probability distribution for yield or other phenotypic traits of the variety candidates in the growing conditions of the TPE directly by constructing an agronomic optimisation objective function in which the other parameters of the agronomic optimisation objective function are data about a set of one or more existing fields in the TPE used for the cultivation of the crop species to which the plurality of chosen lines belong to, field size information for the set of one or more existing fields in the TPE and data about the total amount fields and their uses in the TPE. The values of the first set of one or more environmental parameters are estimated for each field in the set of one or more fields. The selection score function which comprises such an agronomic optimisation objective function at least partially solves the problem above. For each variety candidate g of the plurality of chosen varieties, the selection score function can be determined as $$p(yield_g|TPE) \approx \Sigma_f^F P_f \times p(yield_g|f)$$

or, $$p(yield_g|TPE) = \Sigma_f^F P_f \times \int_{\theta_f} p(yield_g|\theta_f) \times p(\theta_f) d\theta_f \qquad (2)$$

where in Equation 2, $f \in 1, \ldots, F$, are fields in the set of one or more fields, $\theta_f$ are the values of the first set of one or more environmental parameters related to each field f, $p(\theta_f)$ is the probability distribution of the values of the first set of one or more environmental parameters for each field f of the set of fields. The probability distribution may be estimated from historical records, climate simulations, user-defined simulation or weather forecasts, $p(yield_g|\theta_f)$ is the probability distribution for yield obtained from the prediction model under conditions corresponding to $\theta_f$ for variety g, and $P_f$ is the proportion of the area of the field f of the total field area of the TPE.

It may be understood that the program, or the plurality of program modules can implement the mathematical Equation 2 in the agronomic optimisation objective function and process the first set of one or more environmental parameters, the received set of phenotype information, the received set of environmental information and the optionally received genotype information, to compute selection score values for lines to be used in a breeding program.

The present disclosure provides also a system for selecting a plant variety for cultivation in a target area. The system relates to arrangement including programmable and/or non-programmable components that is configured to select a plant variety based on the selection score value for cultivation in the target area. Furthermore, the programmable and/or non-programmable components are configured to efficiently acquire, store, process information available. Optionally, the programmable and/or non-programmable components are arranged in a manner to form a computing environment, such as a centralized computing environment and/or a distributed computing environment that can select the plant variety having the best performance in terms of the selection score when cultivated in the target area. Throughout the present disclosure, the term "system" relates to an arrangement comprising several devices and/or parts that interact with one another.

The system comprises a data processing arrangement. The data processing arrangement includes at least one programmable or computational entity configured to perform specific tasks associated with the system. Specifically, the data processing arrangement is configured to host computer programs and/or routines that is operable to perform specific tasks associated with the system. Optionally, the data processing arrangement can be a single computational entity and/or plurality of computational entities operating in a parallel or distributed architecture to perform the specific tasks associated to the system. Optionally, the data processing arrangement can be implemented as a computer program that provides various services (such as database service) for the system.

Generally, the computer programs may implement artificial intelligence and machine learning based algorithms for estimating the environmental parameters over a period of time.

Furthermore, the historical data related to weather conditions associated with the target area may relate to weather data stored in the data processing arrangement. Optionally, the historical data related to weather conditions stored in the data processing arrangement is acquired and curated by one or more computer programs and/or routines hosted in the data processing arrangement. Furthermore, the historical data related to weather conditions or other environmental parameters can be acquired from the third-party service provider. Optionally, the historical data related to weather conditions or other environmental parameters includes information associated with the one or more environmental parameters that affects the natural environment (namely, individual measured values or time series of measured values of one or more environmental parameters) of the target area for a specific time duration (such as one year). Optionally, the values of the first set of one or more environmental parameters are estimated in a user-defined simulation of the target area by modifying at least one of the environmental parameter values of an observed experiment. For example, more rain can be added to the conditions of an observed experiment by increasing the values of environmental parameters associated with rain while otherwise maintaining the values of the environmental parameters that were observed in the experiment.

Optionally, the computer programs and/or routines include one or more prediction algorithms therein. These prediction algorithms may be for example related to the above-mentioned climate simulation or weather forecast. The prediction algorithms are set of instructions that are operable to analyse the historical data related to weather conditions, and subsequently estimate one or more environmental parameters over a predefined future period of time for the target area.

Optionally, the data describing the environmental parameters can be acquired by the data processing arrangement from a third-party service provider. The third-party service provider refers to one or more systems, applications, and/or a combination thereof for providing electronic content (namely, the data describing the parameters that affect the natural environment of the target area) to the data processing arrangement via a data network. Furthermore, the third-party service provider may be subscription based, i.e. the data describing the parameters of the target area is provided as an online service that is accessed by the data processing arrangement with subscriber accounts.

Optionally, the data describing the parameters that is accessed from the third-party service provider by the data processing arrangement includes information describing effects of the parameters on the natural environment of the target area for a specific time duration. For example, the third-party service provider may include curated information related to the effects of the parameters on the natural environment of the target area for past one year. In such example, the curated information related to the effects of the parameters on the natural environment of the target area for past one year (or several years) may be described as the growth ratio of one or more plant varieties for past one year (or several years) upon being exposed to various environmental parameters or conditions.

In an example, the historical data related to weather conditions associated with the target area for predefined past period of time (such as, but is not limited to, the growing seasons for the crop plant under study during the last 10 years) provides that the temperature for the target area remains in a range of 20 to 30° Celsius, the rain fall for the target area remains in a range of 2 to 6 mm/week, the air humidity for the target area remains in a range of 30 to 35%, the carbon dioxide content for the target area remains in a range of $10^{-6}$ to $10^{-8}$ mol $CO_2$ per mol, the soil composition is such that it contains 20-40% of sand, 20-40% of silt, 20-40% of clay and 5-15% of organic content, the soil nutrient concentrations for the target area remain in certain nutrient-specific ranges, the soil moisture at 20 cm depth for the target area remains in a range of 20 to 30%, the wind velocity for the target area remains in a range of 25 to 30 km/h, the wind variability for the target area remains in a range of 25 to 70%, the radiation intensity and spectrum for the target area remains in a range of 10 W/sr to 30 W/sr, and the plant diseases for the target area include blights, cankers and rots.

In such example, the prediction algorithms may be operable to determine that for the predefined future period, the temperature for the target area remains in a range of 18° to 32° Celsius, the rain fall for the target area remains in a range of 1 mm to 7 mm/week, the air humidity for the target area remains in a range of 30% to 40%, the carbon dioxide content for the target area remains in a range of $10^{-6}$ to $10^{-8}$ mol $CO_2$ per mol, the soil composition for the target area includes 10 to 17 nutrients (such as manganese, zinc, copper, and iron), the soil nutrient concentrations for the target area remains in a range of 50 to 80%, the soil moisture for the target area remains in a range of 20 to 25%, the wind velocity for the target area remains in a range of 20 km/h to 30 km/h, the wind variability for the target area remains in a range of 25% to 60%, the radiation intensity and spectrum for the target area remains in a range of 10 W/sr to 30 W/sr, and the plant diseases for the target area may possibly be blights, cankers and rots.

The present description still further relates to use of a system as described above with a prediction model to simulate variety and/or line performance under conditions that were unobserved in the field trials. Indeed, the prediction model can be used to evaluate relative variety/line performance under conditions that were not observed in any of the performed field trials where the varieties/lines were studied. A first step consists of selecting values for the first set of environmental parameters corresponding to conditions, under which variety/line performance should be evaluated. Then those parameter values are entered as input in the prediction model along with other model parameter values, and the model outputs variety/line-specific performance under the conditions corresponding to the input values of the first set of environmental parameters. In this way the impact of drought and heat stress and other environmental conditions can be evaluated.

An example of the present disclosure and its working is given in an article titled "Modelling G×E with historical weather information improves genomic prediction in new environments", published at https://www.biorxiv.org/content/early/2017/11/03/213231, The article was part of the priority application and published after the priority date. The article is thus hereby incorporated by reference to this application in its entirety.

DETAILED DESCRIPTION OF THE DRAWINGS

Referring to FIG. 1, is a block diagram of a system 100 for selecting a plant variety for cultivation in a target area, in accordance with an embodiment of the present disclosure. The system 100 comprises a data processing arrangement 102 and a cloud service 108. The data processing arrangement 102 includes a data storage unit 104. It will be appreciated that the data storage unit 104 is associated with the cloud service 108, such that the data storage unit 104 is configured to store information and enables retrieving of the stored information for processing thereof. The data processing arrangement 102 further includes a prediction model 106. The prediction model 106 comprises information about growth of different plant varieties in relation to different environmental parameters, and wherein the selection score is determined by processing the estimated one or more environmental parameters and received set of phenotype information and the received set of environmental information and the optionally received genotype information in the acquired prediction model. Optionally, the data processing arrangement 102 is further configured to generate the prediction model 106 by implementing machine learning and artificial intelligence-based algorithms and using historical data related to one or more environmental parameters affecting growth of plant varieties with different genotypes. In some examples, the prediction model 106 may be stored in the data storage unit 104, of the data processing arrangement 102. Further, as illustrated in FIG. 1, the data processing arrangement 102 may be connected to one or more sensors, such as sensors 110a, 110b and 110c disposed in a target area 10. These sensors 110a, 110b and 110c may include sensors for temperature, rain fall, air humidity, carbon dioxide content, soil composition, soil moisture, soil nutrient concentrations, plant diseases, wind velocity, wind variability, radiation intensity and spectrum, etc.

As shown, the data processing arrangement 102 is communicably coupled to the cloud service 108. Optionally, the data processing arrangement 102 is communicably coupled to the cloud service 108 using a communication network. In an example, the communication network can be a cellular network, short range radio (for example, such as Bluetooth®), Internet, a wireless local area network, and an Infrared Local Area Network, or any combination thereof. In an embodiment, the cloud service 108 may be an internet, a host of computers or a third-party service provider. Optionally the cloud service 108 can enable the communication with the third-party service provider.

The data storage unit 104 is operable to store the data related the received set of phenotype information, the received set of environmental information, the estimated first set of one or more environmental parameters, the optionally received genotype information and the selection score values of a plurality of plant varieties.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for selecting a plant variety from a plurality of chosen plant varieties for cultivation in a target area, the plant variety having at least one phenotypic trait, the method comprising:
    selecting a selection score function, which selection score function uses as input at least one prediction of one or more phenotypic traits and one or more additional selection score parameters and which selection score function is configured to output a selection score value for a plurality of chosen plant varieties;
    estimating values of a first set of one or more environmental parameters for a predefined future period of time for the target area;
    receiving
        a set of phenotype information comprising phenotypic trait measurements for a first sub-set of a plurality of plant varieties; and
        a set of environmental information comprising values of a second set of one or more environmental parameters for said first sub-set;
    determining a prediction model for the phenotypic traits, based on the estimated values of the first set of one or more environmental parameters, the received set of phenotype information and the received set of environmental information;
    using the prediction model to output predictions for phenotypic traits for the plurality of chosen plant varieties;
    using the selection score function to compute selection score values based on the predictions for phenotypic traits for the plurality of chosen plant varieties and one or more additional selection score parameters; and
    selecting at least one plant variety to be cultivated in the target area from the plurality of chosen plant varieties, based the computed selection score values of the plurality of chosen plant varieties.

2. The method according to claim 1, further comprising receiving genotype information of one or more of the plant varieties of the plurality of plant varieties and using the genotype information in the prediction model for the phenotypic traits.

3. The method according to claim 1, wherein the prediction model comprises
    a variety specific main effect prediction model, configured to predict the effect of each plant variety on phenotypic traits by processing the received set of phenotype information and optionally the received environmental information and optionally the received genotype information;
    a genotype-environment interaction model, configured to predict differences between phenotypic traits of plant varieties of the plurality of chosen plant varieties in relation to the first set of environmental parameters by processing the received set of phenotype information and the received set of environmental information and optionally the received genotype information and the values of the first set of environmental parameters; and
    an environment-specific effect prediction model configured to predict the effect of each environment on the phenotypic traits by processing the received phenotype information and optionally the received genotype information and optionally the received environmental information and the values of the first set of environmental parameters.

4. The method according to claim 1, wherein the selection score function is based on the prediction for one or more phenotypic traits from the prediction model and further comprises
    an agronomic optimisation objective function for processing one or more phenotypic trait predictions and optionally a set of other parameters for the agronomic optimisation objective function; and
    a probability distribution associated with the other parameters of the agronomic optimisation objective function.

5. The method according to claim 1, wherein the one or more environmental parameters comprise one or more of temperature, rain fall, air humidity, carbon dioxide content, soil composition, soil moisture from at least one depth, soil temperature from at least one depth, soil nutrient concentrations, disease pressures of different plant diseases, wind velocity, wind variability, radiation intensity and radiation spectrum.

6. The method according to claim 1, wherein the values of the one or more environmental parameters of the first set of environmental parameters are estimated based on at least one of historical data related to weather conditions associated with the target area, climate simulation associated with the target area, user-defined simulation and weather forecast associated with the target area.

7. The method according to claim 1, wherein the genotype information comprises at least one of genealogy of the plant variety, Single Nucleotide Polymorphism measurements of the plant variety, sequencing measurements of the plant variety and epigenetic measurements of the plant variety.

8. The method according to claim 1, wherein the predefined future period of time corresponds to at least one growing season for the one or more chosen plant varieties.

9. The method according to claim 1, wherein the selected plant variety is one from the one or more chosen plant varieties with the highest value of the selection score.

10. The method according to claim 1, wherein the phenotypic traits of the plant variety correspond to at least one of yield, yield components, root traits, quality traits such as protein content and taste, growth speed and sensitivity to diseases of the plant variety.

11. A method for selecting a plant line for field trials in a plant breeding program aiming at producing new varieties for the target area, the plant line having at least one phenotypic trait, the method comprising:
   selecting a selection score function, which selection score function uses as input at least one prediction of one or more phenotypic traits and one or more additional selection score parameters and which selection score function is configured to output a selection score value for a plurality of chosen plant lines;
   estimating values of a first set of one or more environmental parameters for a predefined future period of time for the target area;
   receiving
      a set of phenotype information comprising phenotypic trait measurements for a first sub-set of a plurality of plant lines; and
      a set of environmental information comprising values of a second set of one or more environmental parameters for said first sub-set;
   determining a prediction model for the phenotypic traits, based on the estimated values of the first set of one or more environmental parameters, the received set of phenotype information and the received set of environmental information;
   using the prediction model to output predictions for phenotypic traits for the plurality of chosen plant lines;
   using the selection score function to compute selection score values based on the predictions for phenotypic traits for the plurality of chosen plant lines and one or more additional selection score parameters; and
   selecting at least one plant line to be tested in a field trial to develop a new variety for the target area from the plurality of chosen plant lines, based the computed selection score values of the plurality of chosen plant lines.

12. A system for selecting a plant variety for cultivation in a target area, the system comprising a data processing arrangement configured to:
   the plant variety having at least one phenotypic trait, the method comprising:
      select a selection score function, which selection score function uses as input at least one prediction of one or more phenotypic traits and one or more additional selection score parameters and which selection score function is configured to output a selection score value for a plurality of chosen plant varieties;
      estimate values of a first set of one or more environmental parameters for a predefined future period of time for the target area;
      receive
         a set of phenotype information comprising phenotypic trait measurements for a first sub-set of a plurality of plant varieties; and
         a set of environmental information comprising values of a second set of one or more environmental parameters for said first sub-set;
      determine a prediction model for the phenotypic traits, based on the estimated values of the first set of one or more environmental parameters, the received set of phenotype information and the received set of environmental information;
      use the prediction model to output predictions for phenotypic traits for the plurality of chosen plant varieties;
      use the selection score function to compute selection score values based on the predictions for phenotypic traits for the plurality of chosen plant varieties and one or more additional selection score parameters; and
      select at least one plant variety to be cultivated in the target area from the plurality of chosen plant varieties, based the computed selection score values of the plurality of chosen plant varieties.

13. The system according to claim 12, wherein the data processing arrangement is further configured to receive genotype information of one or more of the plant varieties of the plurality of plant varieties and use the genotype information in the prediction model for the phenotypic traits.

* * * * *